United States Patent
Silva et al.

(10) Patent No.: US 9,636,159 B1
(45) Date of Patent: May 2, 2017

(54) MULTI-THREAD ILIAC SCREW

(71) Applicants: Octavio Cesar Silva, Melbourne, FL (US); Fernando Emilio Silva, Fort Worth, TX (US)

(72) Inventors: Octavio Cesar Silva, Melbourne, FL (US); Fernando Emilio Silva, Fort Worth, TX (US)

( * ) Notice: Subject to any disclaimer, the term of this patent is extended or adjusted under 35 U.S.C. 154(b) by 0 days.

(21) Appl. No.: 14/499,180

(22) Filed: Sep. 28, 2014

Related U.S. Application Data (60) Provisional application No. 61/897,199, filed on Oct. 30, 2013.

(51) Int. Cl.
*A61B 17/70* (2006.01)
*A61B 17/86* (2006.01)

(52) U.S. Cl.
CPC ........ *A61B 17/863* (2013.01); *A61B 17/7032* (2013.01); *A61B 2017/8655* (2013.01)

(58) Field of Classification Search
CPC ......... A61B 17/7001; A61B 17/7032–17/7046
USPC .......................................... 606/259, 260, 278
See application file for complete search history.

(56) References Cited

U.S. PATENT DOCUMENTS

| | | | |
|---|---|---|---|
| 2006/0100622 A1* | 5/2006 | Jackson | A61B 17/7037 606/304 |
| 2008/0215095 A1* | 9/2008 | Biedermann | A61B 17/7031 606/246 |
| 2009/0024174 A1* | 1/2009 | Stark | A61B 17/8625 606/321 |
| 2010/0160971 A1* | 6/2010 | Glerum | A61B 17/7037 606/278 |

* cited by examiner

*Primary Examiner* — Nicholas Plionis (57) ABSTRACT

The Multi-Thread Iliac Screw represents a novel way to embed fasteners in the ilium by improving fixation of said fasteners in the different parts of the iliac bone tissue. The screw consists of a saddle with a locking screw and fastener with three types of threads to provide a more mechanically stable embedding of the fastener in the iliac bone. The saddle receives a spinal stabilizing rod, which is part of another vertebral mechanical system, and, as such, the saddle provides an anchor point to the stabilizing rod. In another embodiment, the saddle is designed with an integrated rod on its side, which mates to another hollow rod integrated to a cube-shaped connector, thereby replacing the stabilizing rod. The connector provides the interface to the rest of the vertebral mechanical system.

7 Claims, 16 Drawing Sheets

Bone

MULTI-THREAD ILIAC SCREW

CROSS REFERENCE TO RELATED APPLICATIONS

This is a non-provisional patent submittal corresponding to provisional patent application No. 61/897,199 Multi-Thread Iliac Screw, submitted on Oct. 30, 2013.

BACKGROUND OF THE INVENTION

The present invention relates generally to spinal fixation devices and more specifically relates to an iliac screw assembly, having two types of saddle elements to couple spinal stabilization systems.

Spine disorders comprise conditions that result in misaligned and exaggerated curvatures in certain areas. A healthy spine has smooth curves that support the body and allow natural movement in an individual but certain disorders such as lordosis, kyphosis and scoliosis result in abnormalities that produce unnatural stress in individuals. Lordosis causes significant inward curvature in the lower portion of the back while kyphosis causes abnormal outer curvature in the upper back. In addition, scoliosis causes abnormal sideways curvatures that can be characterized as S or C-shaped. A number of mechanical systems correct these disorders by the use of stabilizing rods that are fixed with connectors and screws anchored to the spine bones. These devices force the spine into a position that produces more natural movement thereby relieving the body of mechanical stress. Mechanisms to affix stabilizing rods, using iliac screws and connectors are described herein.

BRIEF SUMMARY OF THE INVENTION

The invention described herein refers to an Illiac screw assembly in which the fastener of the assembly is designed with three threads to improve fixation inside the Illiac bone tissue. Two embodiments are described wherein the first one consists of an assembly composed of a saddle and a fastener. In this case, the screw assembly is integrated by clipping the fastener inside the saddle in a spherical seat where the fastener head resides and is free to move through broad angles. The screw assembly is used to fixate spine stabilizing rods to the Iliac bone and said rod connects to another vertebral member on the other side. The saddle is designed with a U-shaped groove to accept the stabilizing rod.

The second embodiment consists of the same fastener but in this case the saddle has an integrated rod that extends from its side. This rod is inserted into another hollow rod, which is integrated to a cube connector on the other side, and, by way of this assembly, both rods replace the stabilizing spine rod described in the first embodiment. The cube connector receives the vertebral member, which is part of the spine stabilization system. The saddle rod and the hollow rod slide with respect to each other to attain a desired distance, and, once this is selected, the length is maintained by locking screws that are inserted in the hollow rod.

DETAILED DESCRIPTION OF THE INVENTION

Figure 1:
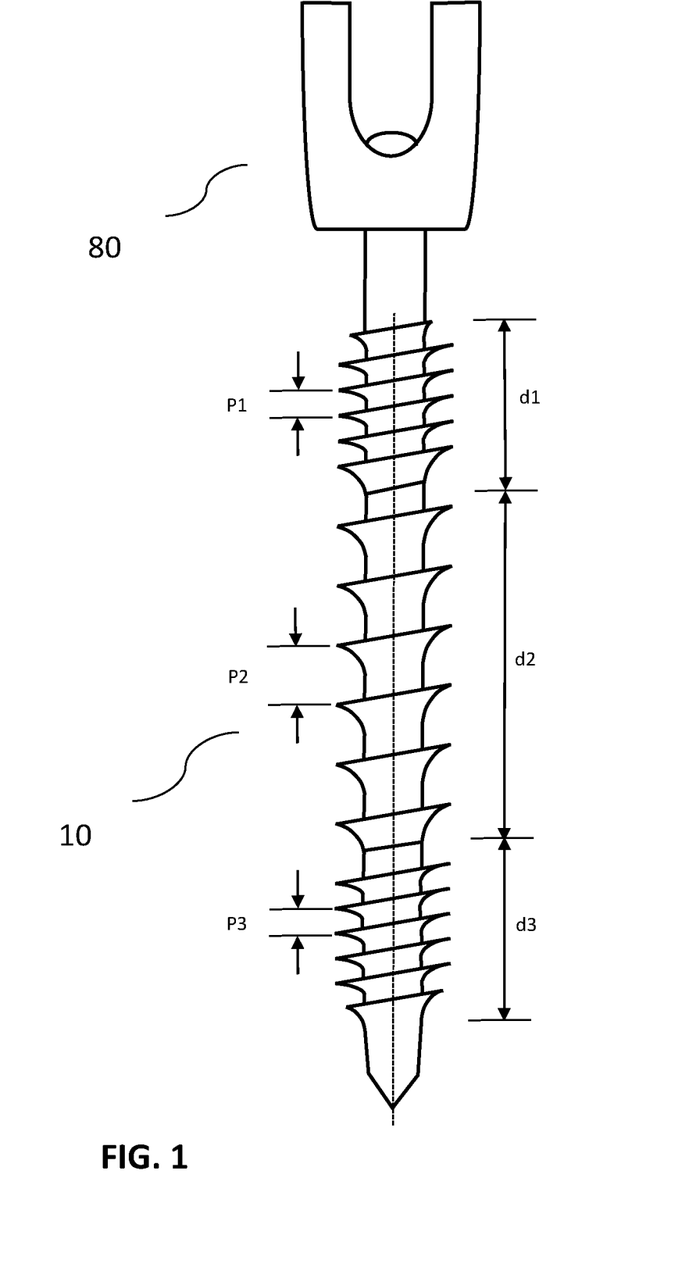
FIG. 1 shows embodiment 1 of the Multi-Thread Iliac Screw design.

FIG. 1 shows embodiment 1 of the Multi-Thread Iliac Screw, consisting of a fastener 10 and a saddle 80 around which the fastener body rotates. The assembly is integrated by inserting the fastener 10 through the top opening of the saddle 80, said operation being terminated by placing the fastener 10 in a cavity located in the bottom of the saddle. The fastener 10 is retained by a small protrusion extending from the interior wall of the saddle which deforms to allow entry of the fastener as described below. The saddle is designed with a U-shaped groove, used to place spinal rods which are held in place by a locking screw that threads from the top of the saddle. The spinal rods are part of another assembly used to stabilize the spine for treatment of various spine conditions. The saddle 80 and the fastener 10 provide an anchor point for the stabilizing rod whereby the fastener 10 penetrates the Iliac bone and is held in place free of rotation by the force exerted on it by the rod once the rod is locked by the saddle locking screw. The saddle 80 and the fastener 10 are made of a corrosion-free, strong alloy, such as a titanium alloy, that provides stiffness and durability.

Figure 2A:
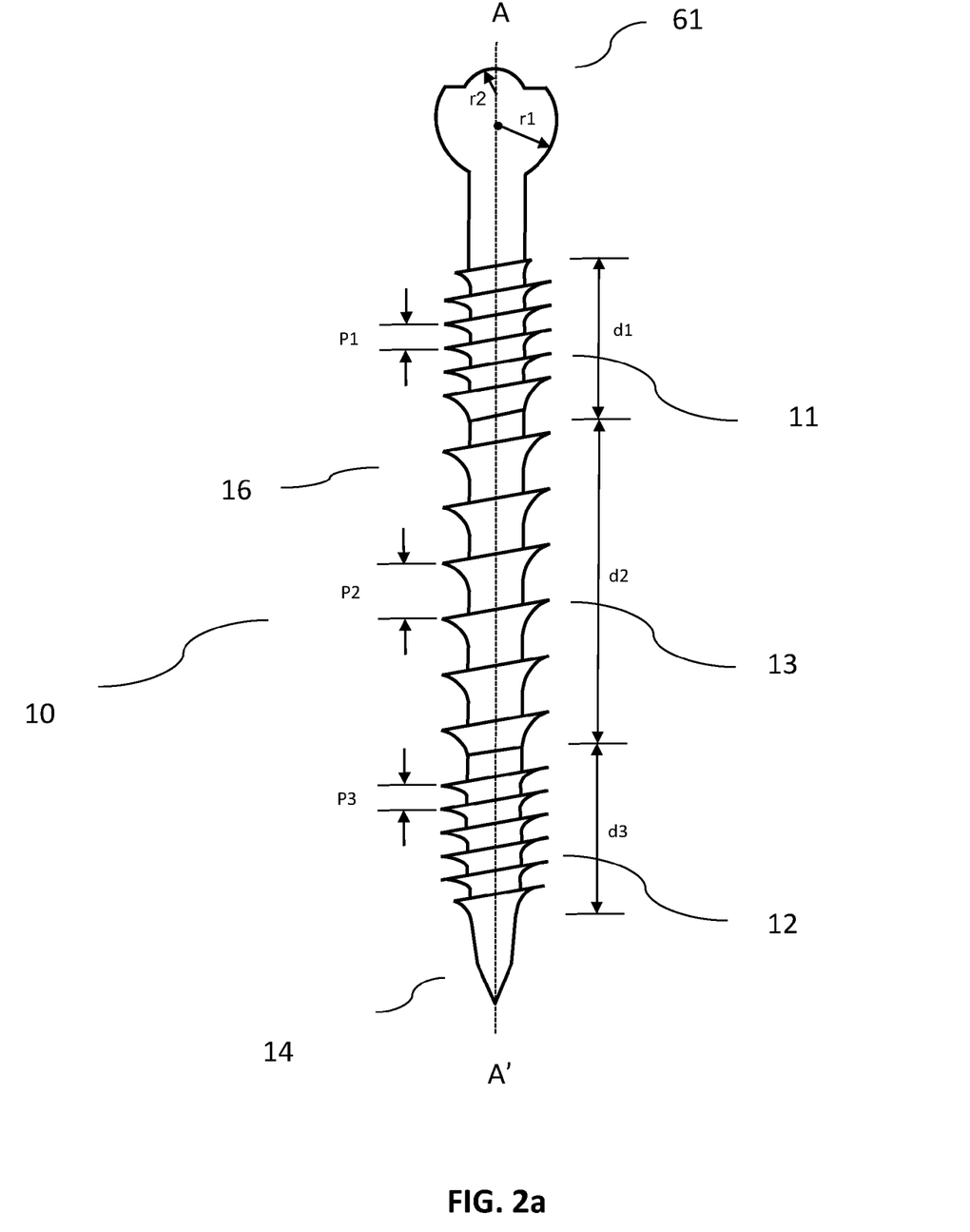
FIG. 2a shows a view of the screw fastener.
Figure 3:
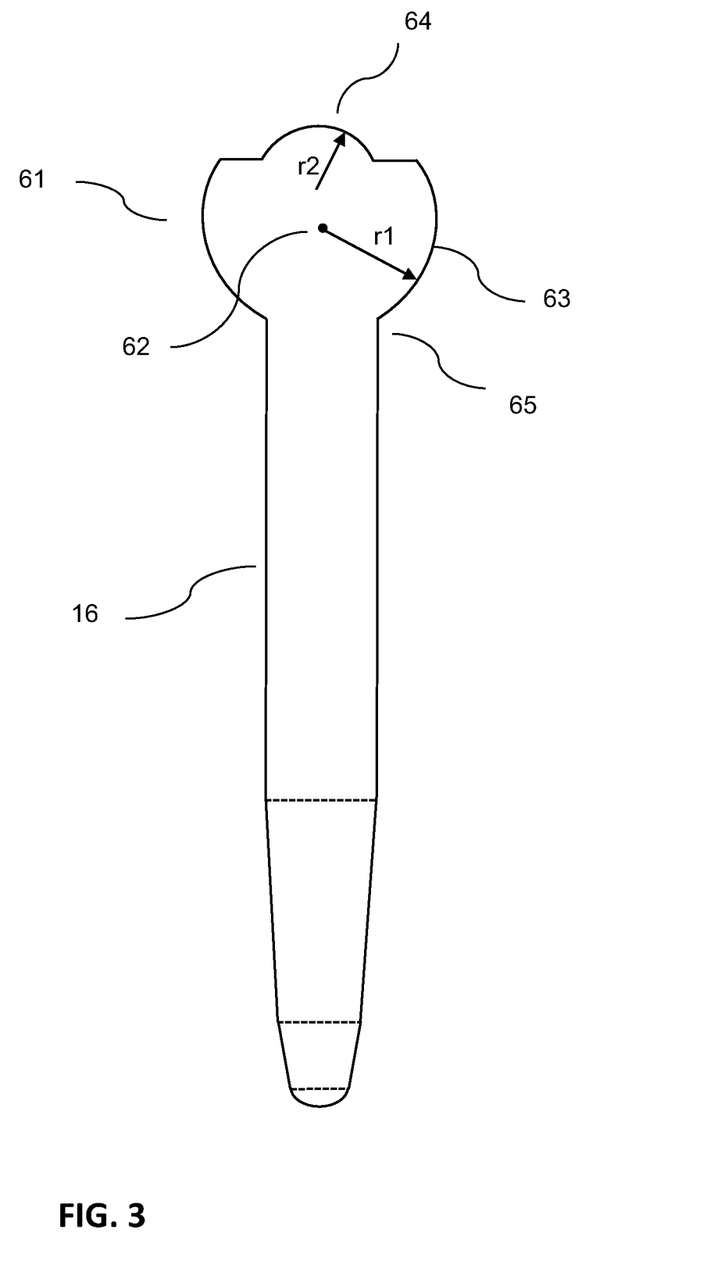
FIG. 3 shows the structure of the fastener head.
Figure 4A:
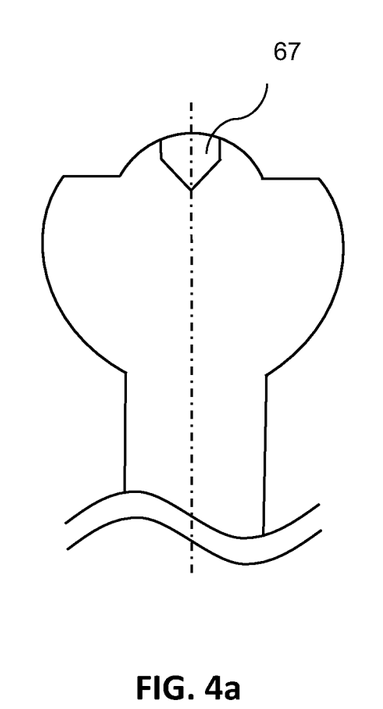
FIG. 4a shows a view of the screw fastener head and its hexagonal bore.
Figure 4B:
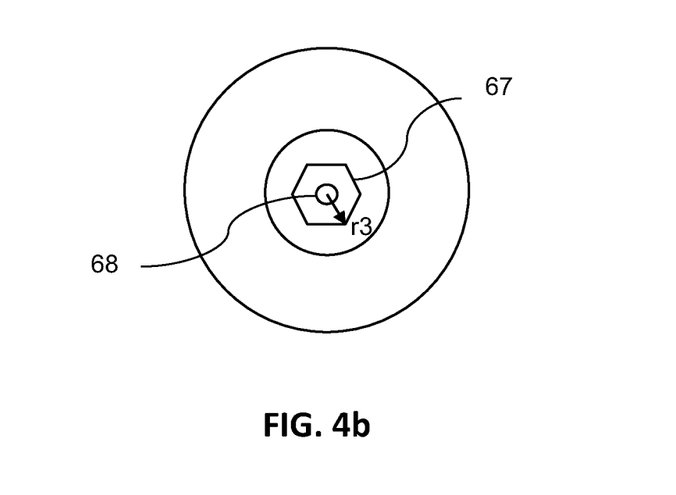
FIG. 4b shows the top view of the fastener head.

The fastener 10 is shown in FIG. 2a and is composed of a head 61, a tip 14 and a body 16 comprised of three threads. The fastener head 61 and the body 16 are symmetrical with respect to longitudinal axis AA'. As shown in FIG. 3, the head 61 is designed with an underside 63 of radius r1 with respect to the center 62 and an upper side 64 composed of a spherical section of radius r2 sitting on a flat surface wherein the spherical section is centered around the A-A' axis and protrudes from the flat surface at a predetermined distance. The upper side 64 is located at a predetermined distance with respect to the bottom of the underside 63. The fastener body 16 is coupled with the head 61 through a curved interface 65. In addition as shown in FIG. 4a, the head 61 provides a hexagonal bore 67 along the longitudinal axis A-A' of the fastener 10 to allow the insertion of a screwdriver with a hexagonal tip in order to insert the fastener 10 into bone tissue. The hexagonal bore 67 is defined by radius r3 as shown in FIG. 4b. Optionally, the fastener 10 can be canulated along the A-A' axis through a bore whose opening 68 is located at the head 61 as shown in FIG. 4b.

As shown in FIG. 2a, the body of the fastener is comprised of three external threads. The proximal thread 11 has a pitch P1; the middle thread 13 has a pitch P2; and the distal thread 12 has a pitch P3. In general, the proximal, middle and distal threads have lengths d1, d2, and d3, respectively.

Figure 2B:
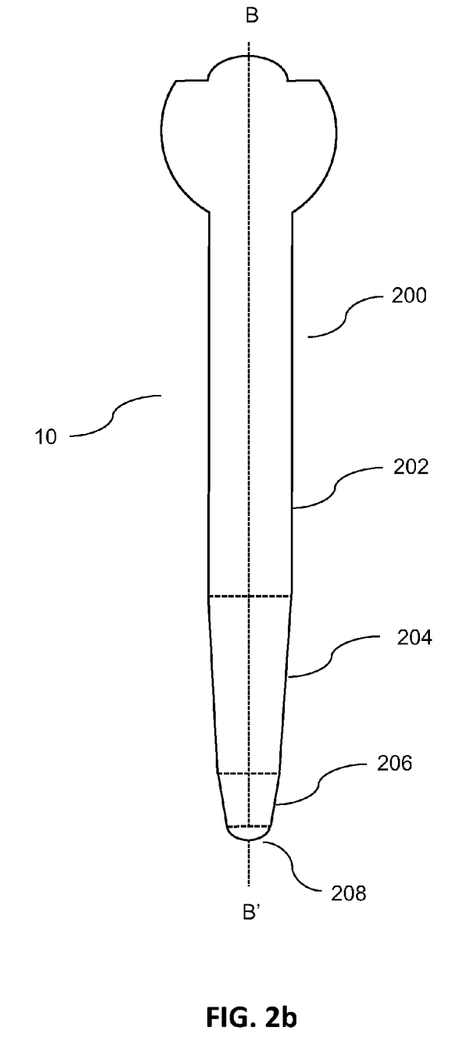
FIG. 2b shows an embodiment of the fastener body.

FIG. 2b depicts an embodiment of the fastener 10 design. The body of the fastener 10 is defined by a shaft 200, which is composed of a non-tapered section 202 of length L1, a first tapered section 204 of length L2, a second tapered section 206 of length L3 and a tip 208. The second tapered section 206 is designed with a tapering greater than that of first tapered section 204. The fastener 10 threads are disposed along these body sections. The body of the fastener 10 may be canulated along axis BB'.

Figure 2C:
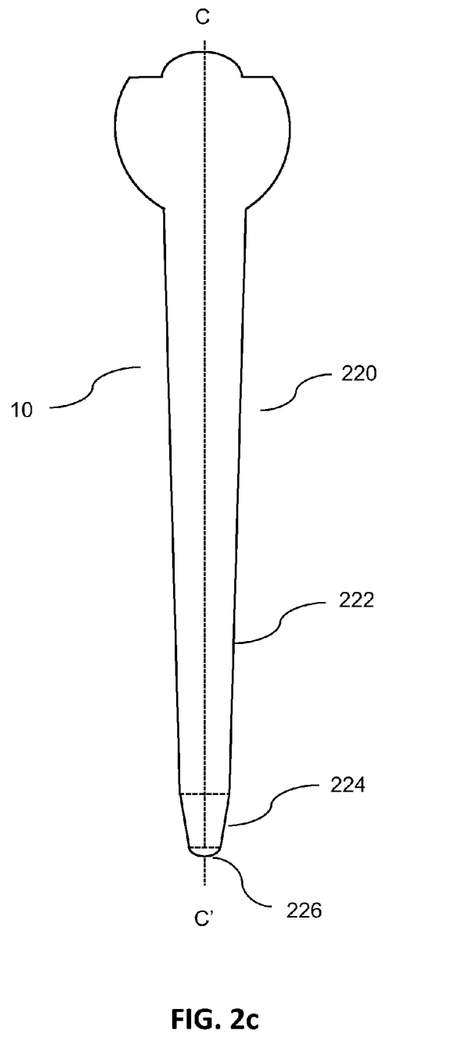
FIG. 2c shows another embodiment of the fastener body.

FIG. 2c depicts another embodiment of the fastener 10 design. The body of the fastener 10 is defined by a shaft 220, which is composed of a first tapered section 222 of length S1, a second tapered section 224 of length S2 and a tip 226. The second tapered section 224 is designed with a tapering greater than that of the first tapered section 222. The fastener 10 treads are disposed along these fastener sections. The body of the fastener may be canulated along axis CC'.

Figure 5A:
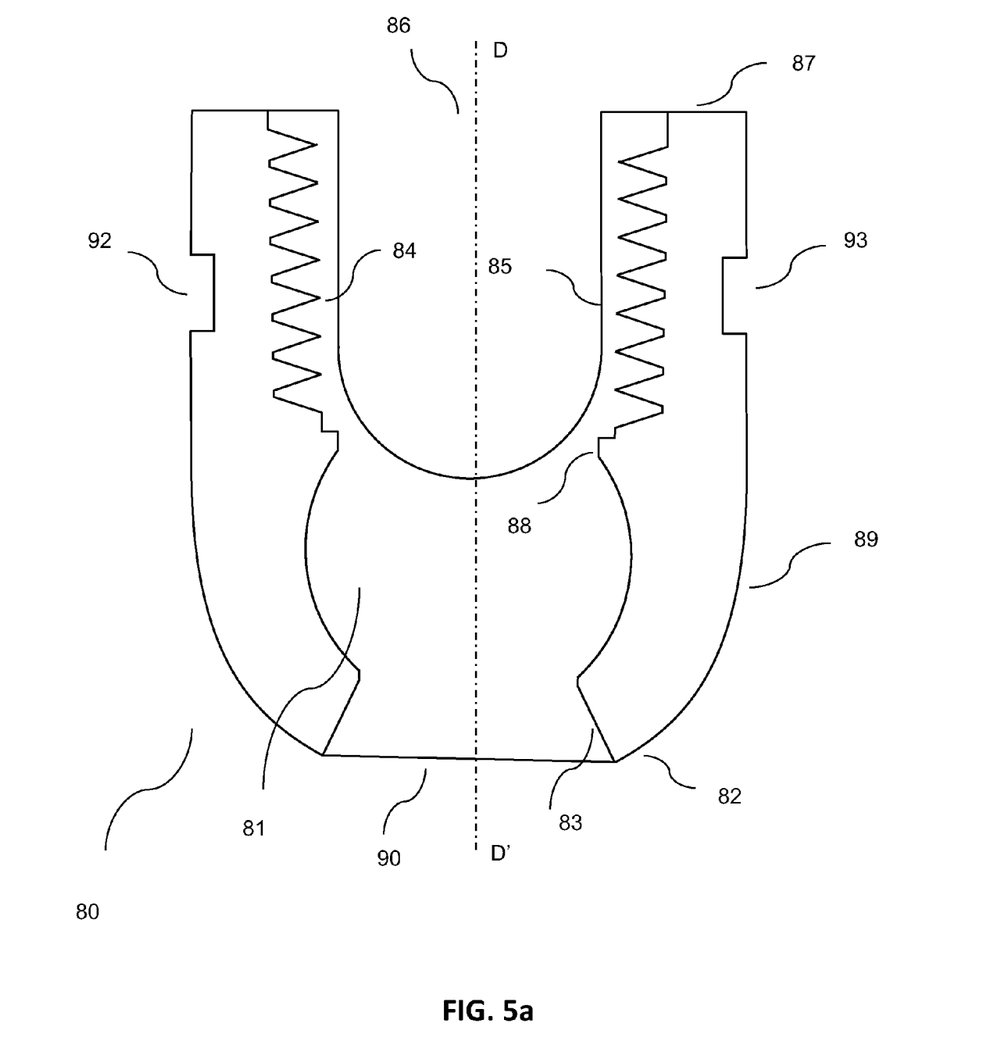
FIG. 5a shows a cross sectional view of the saddle for the screw embodiment 1.
Figure 5B:
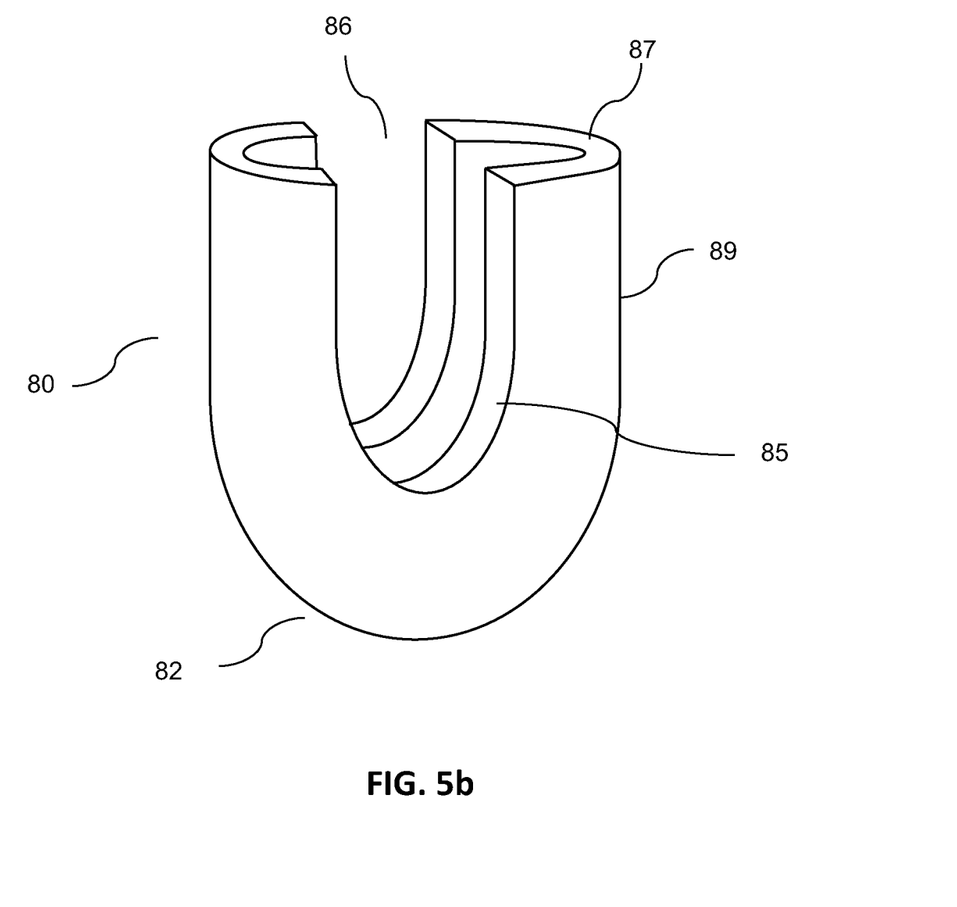
FIG. 5b shows saddle main surfaces for the screw embodiment 1.
Figure 6:
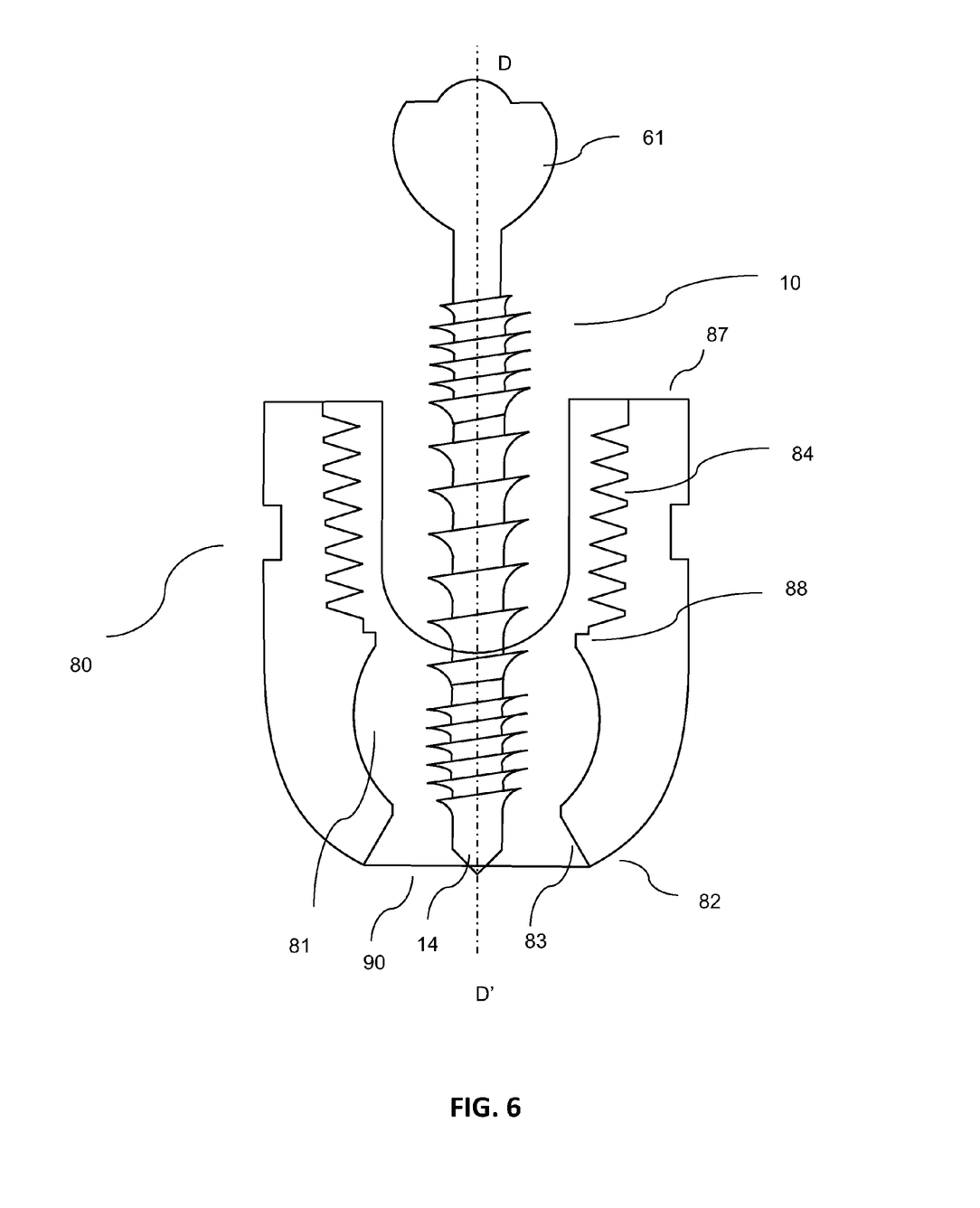
FIG. 6 shows the entry of the screw fastener into the saddle for embodiment 1.

The saddle 80 of embodiment 1 is shown in FIG. 5a. The saddle 80 is defined by an outer surface 89, which terminates in a cylindrical shape at the top 87 and a curved surface at the bottom 82 which also contains a circular opening 90. The saddle 80 is symmetrical with respect to the plane P that passes through the central axis DD' perpendicularly to the cross section of the FIG. 5a. The saddle 80 has a bore 86 with an inner thread 84 that extends downward until the thread 84 terminates at a predetermined distance from the top of the saddle 87. The saddle 80 is designed with a U-shaped groove 85, defined by a U-shaped virtual surface that intersects the saddle 80, that extends downward until it terminates at a predetermined distance from the top 87, allowing the placement of a spine stabilizing rod. Slots 92 and 93 cut parallel to the plane P on the outer surface 89 of the saddle 80 and are used to manipulate the saddle 80 with a surgical tool. The bottom section of the saddle 80 provides an inner chamber 81 with a spherical surface with a radius comparable to that of the fastener head 61 underside 63 and said chamber 81 encases the head 61 of the fastener 10. The main defining surfaces of the saddle are shown in FIG. 5b. The fastener 10, in one method as shown in FIG. 6, is inserted at the top 87, tip 14 first, and it is moved downward until its head 61 clips through the protrusion 88 by deformation inside the saddle inner chamber 81. The underside 63 diameter of the fastener head 61 is less than the diameter of the inner thread 84 except at the protrusion 88, which retains the screw head 61 into position and prevents any upward movement of the fastener head 61. The fastener threaded body 16 comes out of the circular opening 90 at the bottom of saddle and as such the fastener 10 rotates freely through broad angles with respect to the longitudinal axis D-D' of the saddle 80. The bottom of the chamber 81 transitions downward to the circular opening 90 through a short extension 83 that opens at an angle until the bottom 82 is reached.

Figure 7:
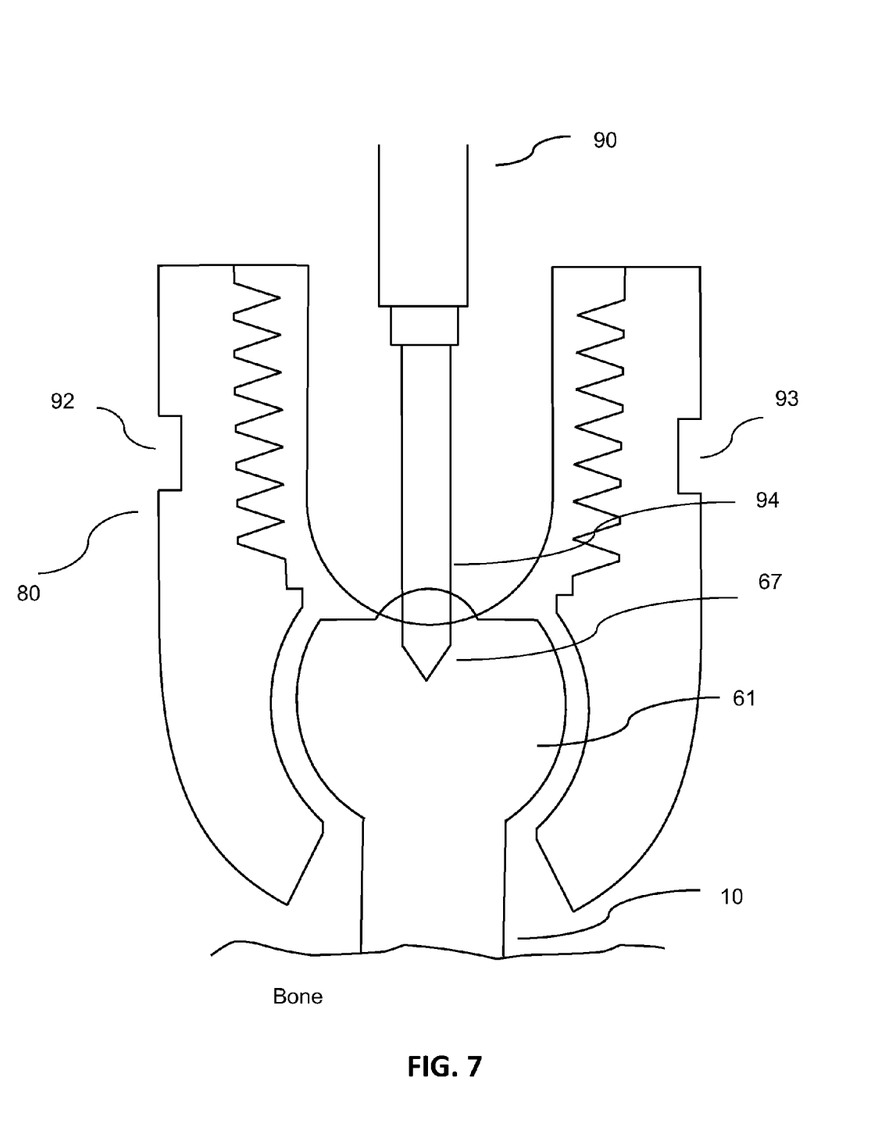
FIG. 7 shows the screw being driven into bone tissue.

Once the saddle 80 and the fastener 10 have been assembled together, the fastener 10 is screwed into bone by a screwdriver 90 with a hexagonal tip 94 as shown in FIG. 7. This tip 94 is inserted in the hexagonal bore 67 at the top of the fastener head 61. The gap left between the saddle 80 lower surface 82 and the bone allows the saddle to rotate freely with respect to the bone and the inserted fastener 10 so that the stabilizing rod can be engaged through several positions. The saddle may be moved by a surgical tool that grasps the saddle outer surface grooves 92 and 93 on both sides.

Figure 8:
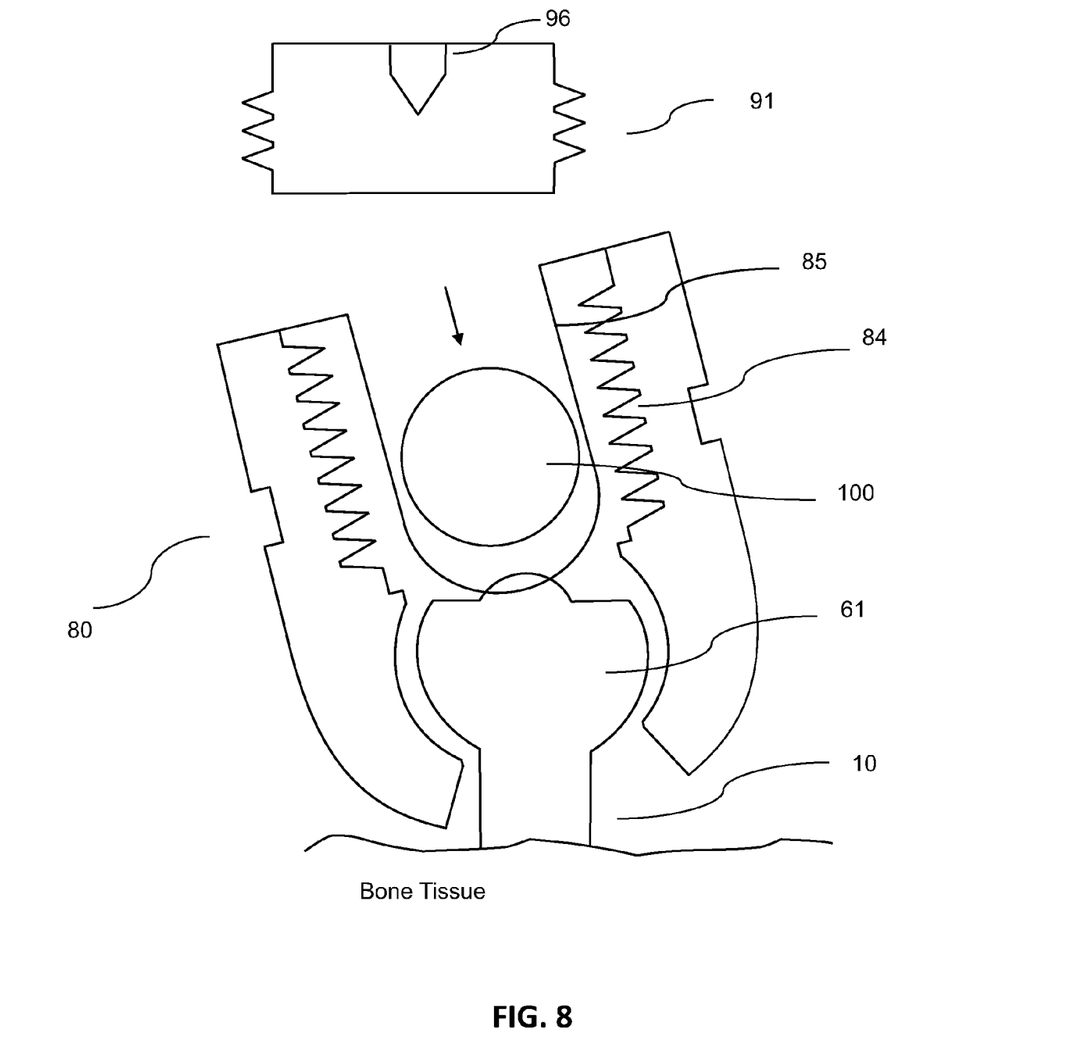
FIG. 8 shows a view of the Illiac Screw with the saddle at an angle and with the spine stabilizing rod placed in the saddle U-shaped groove.

As shown in FIG. 8, once the fastener 10 is put in place inside the saddle 80, and the assembly is screwed into bone tissue, a stabilizing rod 100 is placed in the saddle U-shaped groove 85. Then, a locking screw 91 is threaded along the saddle 80 inner thread 84 until the stabilizing rod 100 is forced next to the fastener head 61. The locking screw 91 is designed with a hexagonal bore 96 to allow reception of a screwdriver with a hexagonal tip. By way of the rod downward force, the fastener 10 is held rigidly into place to prevent any movement with respect to the saddle or the bone tissue.

Figures 9A, 9B:
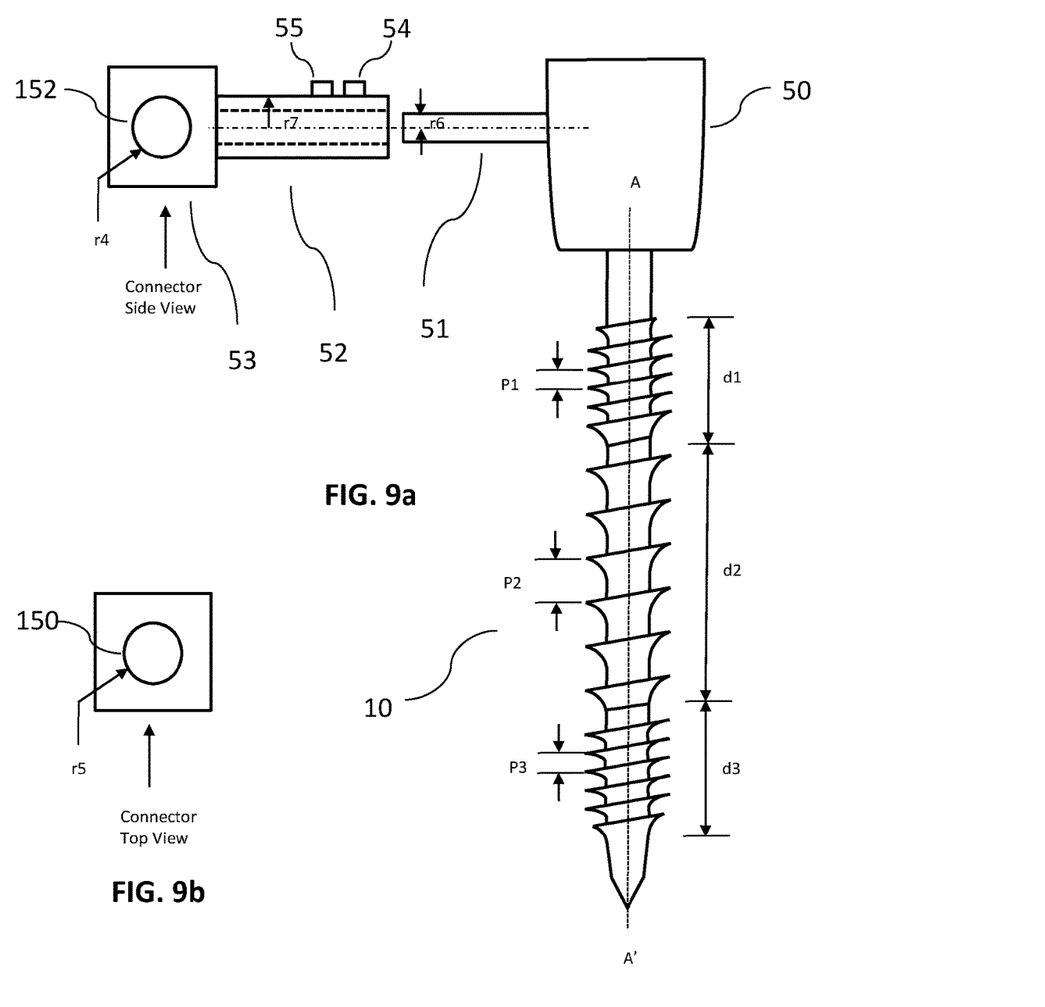
FIG. 9a shows embodiment 2 of the Multi-Thread Iliac Screw design.
FIG. 9b shows the top view of the cube-shaped connector of embodiment 2 of the Multi-Thread Iliac Screw design.
Figure 9C:
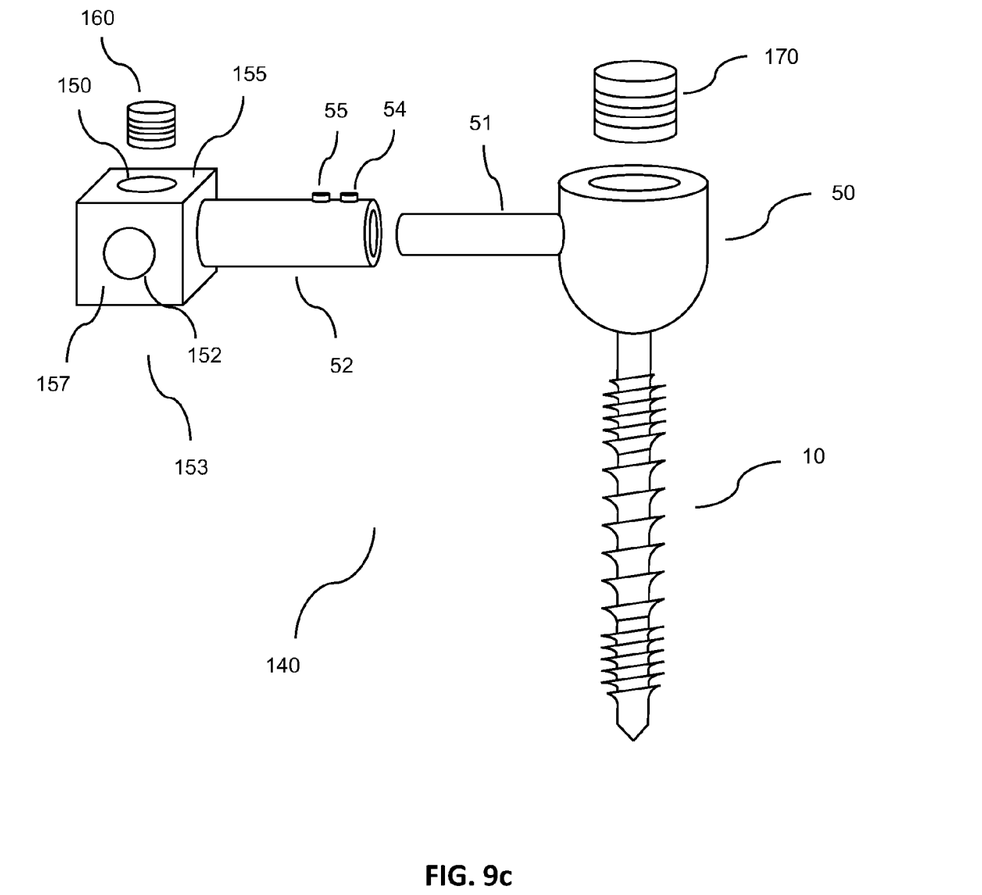
FIG. 9c shows another view of embodiment 2 of the Multi-Thread Iliac Screw design.

Embodiment 2 of the Multi-Thread Iliac Screw 140 is shown in FIG. 9a, FIG. 9b and FIG. 9c. In this design, the body of the fastener 10 is free to rotate in all directions around the saddle 50 but once it is driven into bone tissue a locking screw 170, shown in FIG. 9c, holds the fastener 10 into place free of rotation. A rod 51 of radius r6 is affixed to the side of the saddle 50. This rod 51 slides into a hollow rod 52, of outer radius r7 and inner radius comparable to radius r6, affixed to connector 53, which is cube-shaped. The hollow rod 52 incorporates two locking screws 54 and 55 on top to tighten rod 51 inside of rod 52. In this way, the distance between connector 53 and the saddle 50 can be varied. Rods 51 and 52 replace the stabilizing spine rod 100 described in embodiment 1. Connector 53 contains two perforations. The side perforation 152 with radius r4, shown in FIG. 9a and FIG. 9c, traverses the body of the connector 53 to allow the insertion of a vertebral rod (not shown). The top perforation 150 with radius r5, shown in FIG. 9b and FIG. 9c is threaded so that a locking screw 160, shown in FIG. 9c, can tighten the vertebral rod into position.

Figure 10:
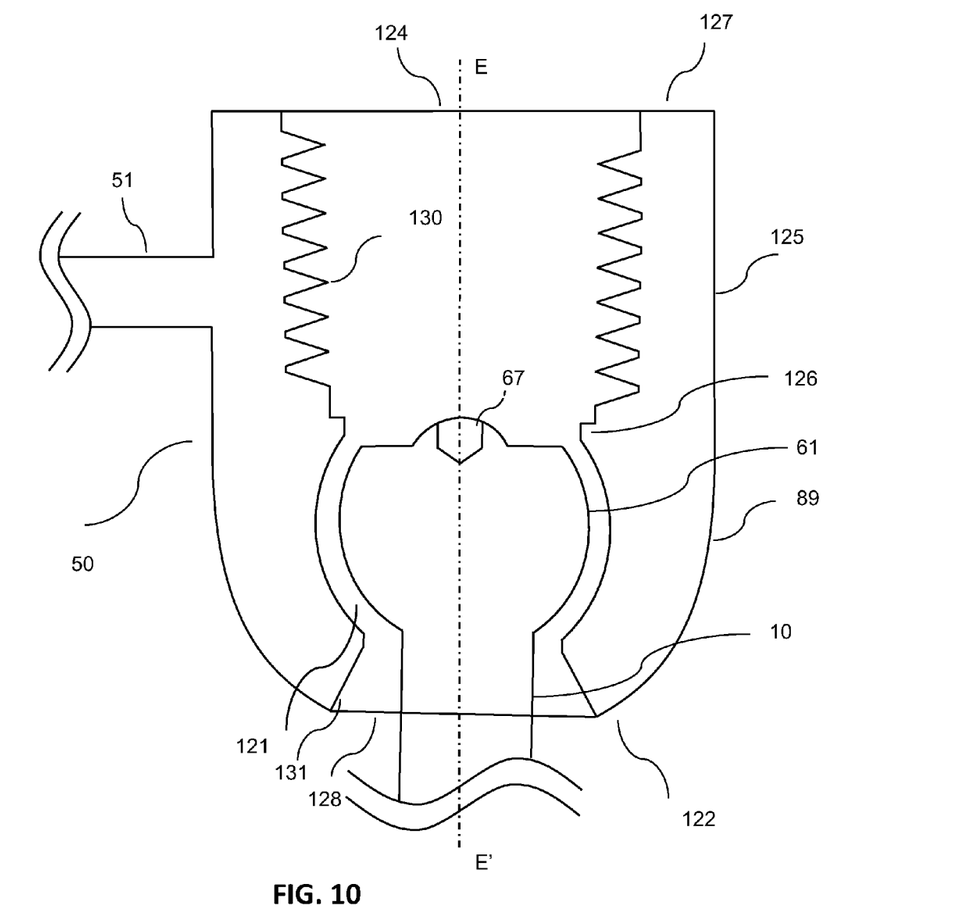
FIG. 10 shows a cross section view of the saddle for embodiment 2.

The saddle 50 of embodiment 2 is shown in FIG. 10. As shown in FIG. 10, the saddle 50 is designed with an outer surface 125, which terminates in a cylindrical shape at the top 127 and a curved surface at the bottom 122, which also contains a circular opening 128. The saddle 50 is symmetrical with respect to the central axis E-E', excluding the extending rod 51. The saddle 50 has a bore 124 with an inner thread 130 that extends downward until it terminates at a predetermined distance from the top 127. The bottom section of the saddle 50 provides an inner chamber 121 with a spherical surface with a radius comparable to that of the underside 63 of the fastener 10 and said chamber encases the head 61 of the fastener 10. Said fastener 10, in one method as in embodiment 1, is inserted at the top 127, tip 14 first, and is moved downward until its head 61 clips by deformation through the protrusion 126 inside the saddle inner chamber 121. The diameter of the fastener 10 underside 63 is less than the diameter of the inner thread 130 except at the protrusion 126, which retains the fastener head 61 into position and prevents any upward movement of the fastener head 61. The fastener threaded body 16 comes out of the circular opening 128 at the bottom of the saddle and as such the fastener 10 rotates freely through broad angles with respect to the longitudinal axis E-E' of the saddle 50. The bottom of the chamber 121 transitions downward to the circular opening 128 through a short extension 131 that opens at an angle until the bottom 122 is reached A screwdriver with a hexagonal tip drives the fastener 10 into bone. The screwdriver enters the saddle 50 through the bore 124 at the top. The fastener 10 has a hexagonal bore 67 in the head for reception of the screwdriver tip.

Figure 11A:
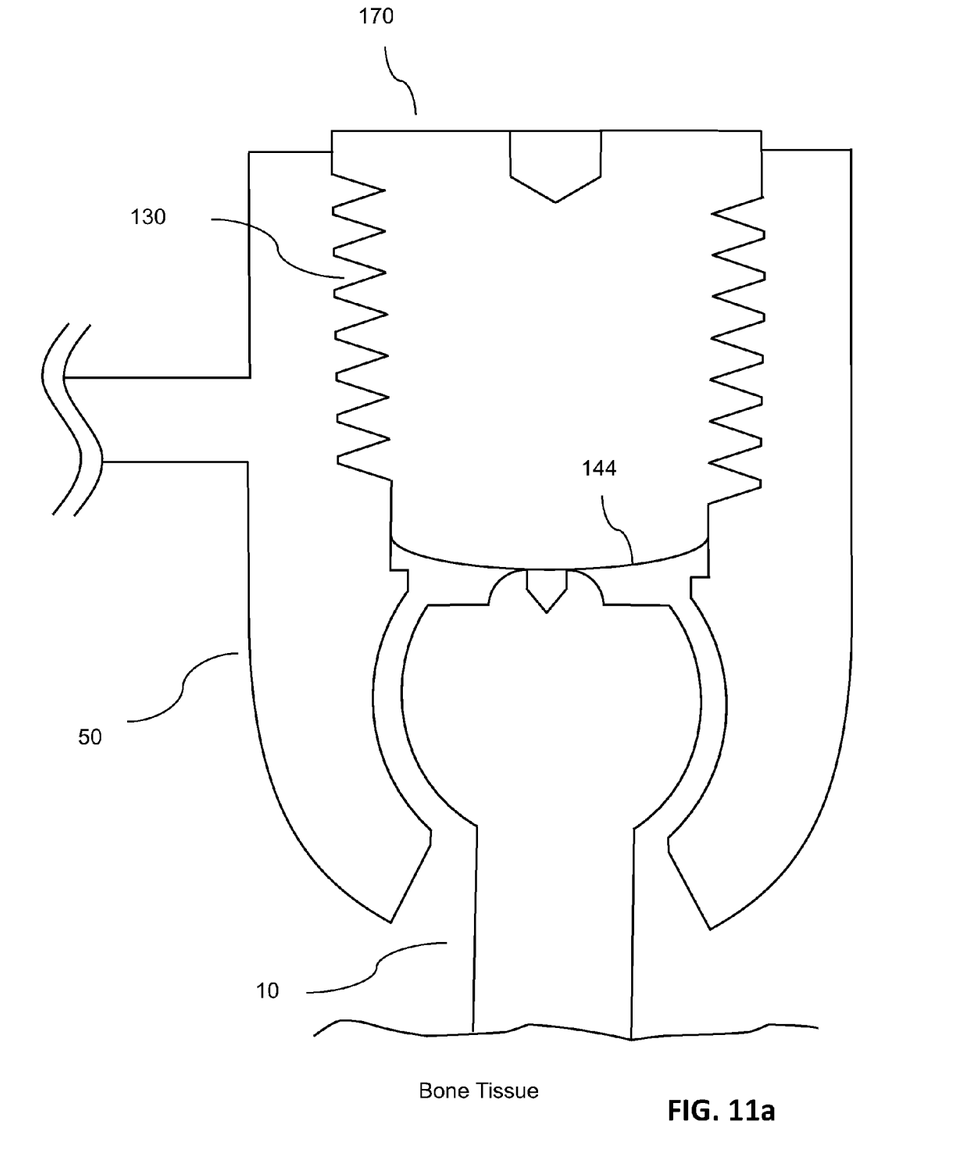
FIG. 11a shows a cross section view of the saddle of embodiment 2 with the fastener in the saddle seat and driven into bone while being held in place with the locking fastener.
Figure 11B:
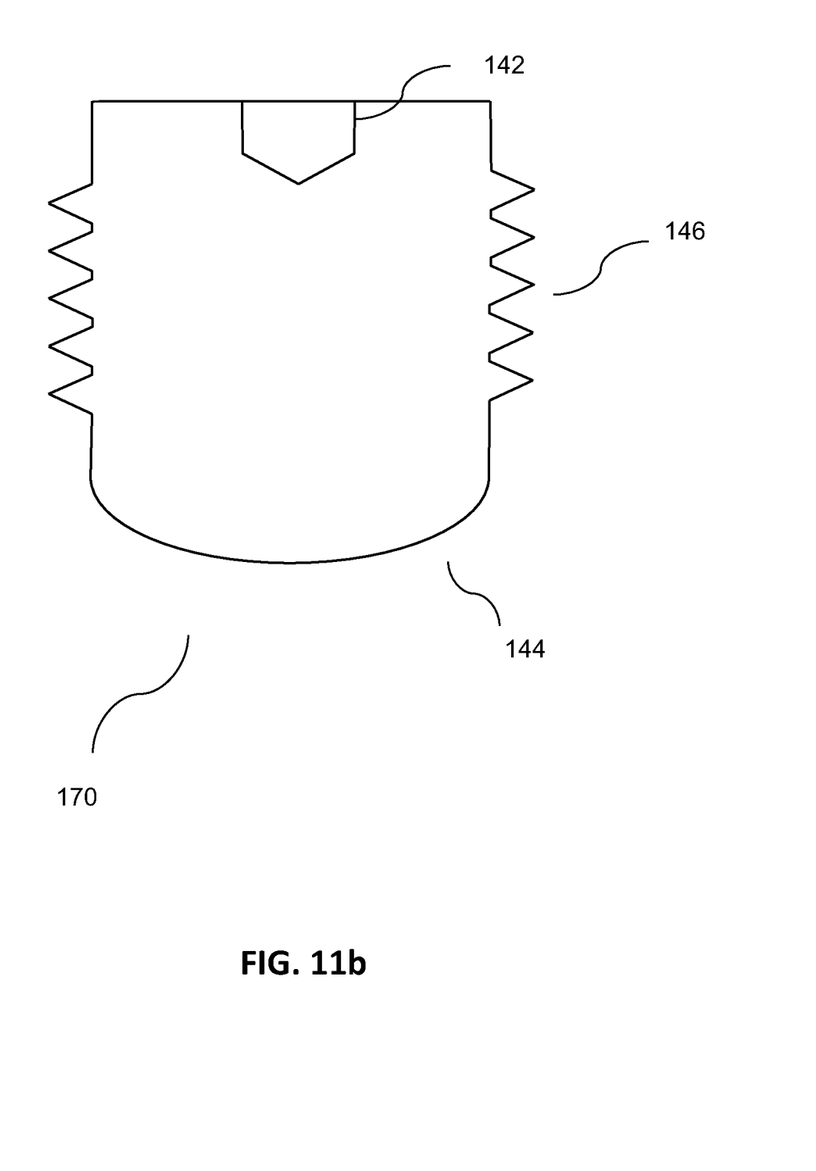
FIG. 11b shows a cross section of the locking fastener of embodiment 2.

As shown in FIG. 11a, once the fastener 10 is put in place inside the saddle 50, and the assembly is screwed into bone tissue, a locking screw 170 is threaded along the saddle inner thread 130 until the it forces the fastener 10 into place. FIG. 11a shows the assembly at a right angle with respect to the bone surface, but the locking screw 170 can hold the screw into position if the saddle 50 is tilted. As shown in FIG. 11b, the locking screw 170 is designed with a hexagonal bore 142 to allow reception of a screwdriver with a hexagonal tip. In addition, the locking screw 170 is designed with a curved surface 144 at the bottom, which provides a contact surface with the fastener 10. By way of the locking screw 170 downward force, the fastener 10 is held rigidly in place to prevent any movement with respect to the saddle 50 or the bone tissue.

Figure 12:
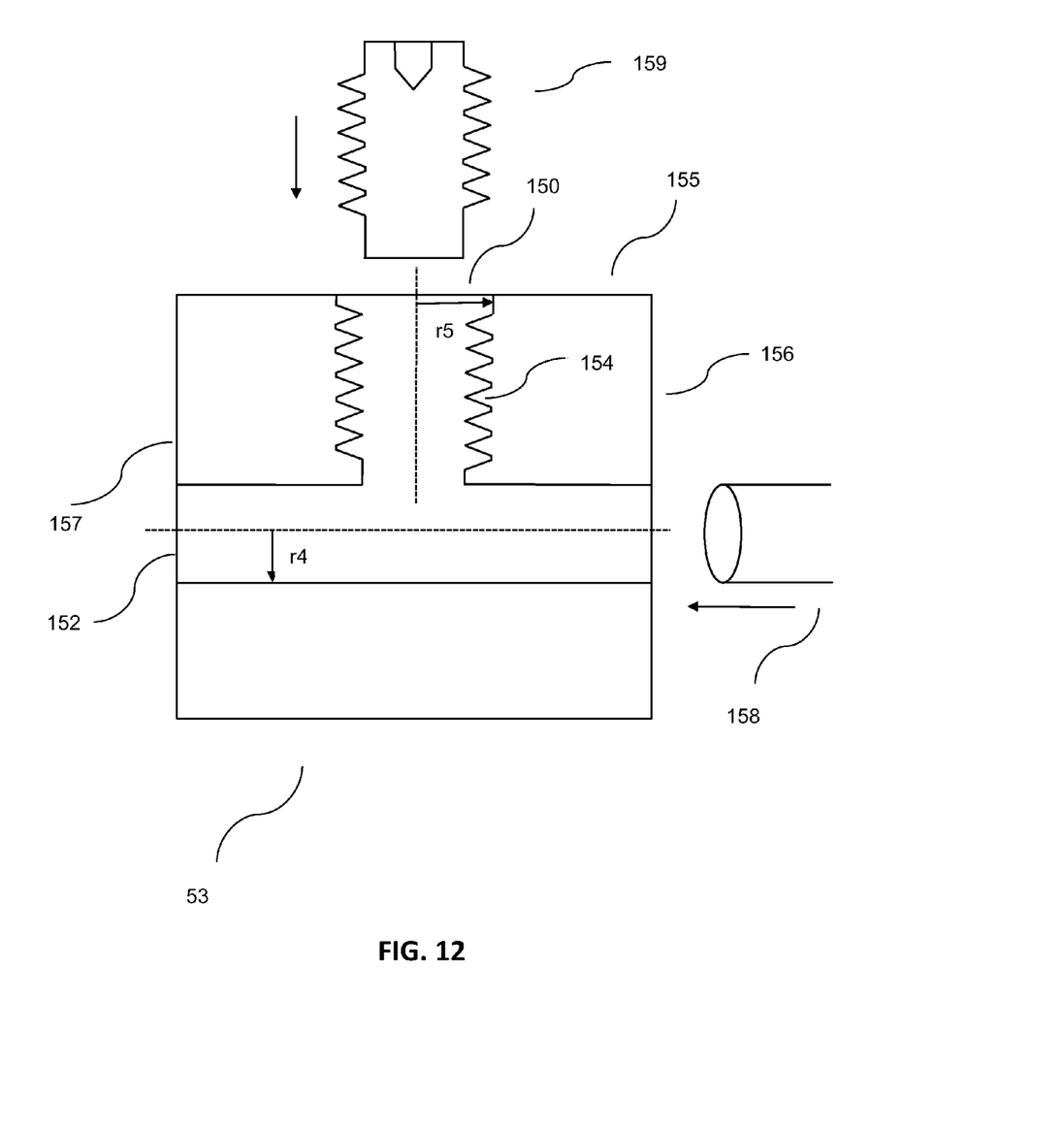
FIG. 12 shows a cross section view of the connector for embodiment 2.

A cross section of connector 53 is shown in FIG. 12. The connector 53 is a cube with a top 155 and a bore 150 with an inner thread 154 that extends to the middle of the cube 53 and has radius r5. A bore 152 with radius r4 and perpendicular to bore 150 extends from side 156 to side 157 of the cube. A vertebral rod 158 enters the bore 152 and is affixed by screw 159, which is threaded through the bore 150. The screw 159 has a hexagonal key 160 for reception of a screwdriver with a hexagonal tip.

The invention claimed is:

1. A Multi-Thread Iliac Screw assembly configured to secure a vertebral rod by extending over to an anchoring point comprising: a saddle consisting of an object with an outer surface, a cylindrical top, a curved bottom, a bore that runs from the top to an inner upper constriction, an inner spherical chamber in the bottom section of said saddle between said upper constriction and a lower constriction wherein both constrictions have circular openings, and an inner thread on the inner wall of said bore; an integrated solid rod affixed to said saddle that projects perpendicularly from said saddle outer surface wherein said solid rod is molded in the same metal piece as that of said saddle comprising the same metal component; a fastener; a saddle locking screw; and a cube-shaped connector with a hollow rod perpendicularly affixed to said cube-shaped connector on the side facing said saddle wherein said hollow rod is molded in the same metal piece as that of said cube-shaped connector comprising the same metal component; wherein said cube-shaped connector is designed with a threaded bore in the middle of the top side, running from the top to the center of the said cube-shaped connector and parallel to the side facing said saddle for reception of a connector locking screw; wherein said cubed-shaped connector is further designed with a horizontal bore that runs through the middle of the cube-shaped connector from the back side to the front side parallel to the side facing the saddle and perpendicularly to said threaded bore on the top side; wherein said integrated rod affixed to said saddle slides, at a predetermined distance, into said hollow rod affixed to said cube-shaped connector by means of a telescoping mechanism; wherein said hollow rod is designed with two locking screws to retain said integrated rod affixed to said saddle; wherein said saddle is located at said anchoring point; wherein the distance between said cube-shaped connector and said saddle can be adjusted by at least two centimeters by said telescoping mechanism of said hollow rod and said solid rod; wherein the outer diameter of said hollow rod is approximately between five millimeters and twelve millimeters; wherein the inner diameter of said hollow rod is approximately between three millimeters and ten millimeters; wherein the diameter of said solid rod is approximately between three millimeters and ten millimeters; wherein the length of a side of said cube-shaped connector is approximately between seven millimeters to sixteen millimeters; wherein the height of said saddle is approximately between five millimeters to sixteen millimeters; and wherein the top outer diameter of said saddle is approximately between five millimeters to sixteen millimeters.

2. The Multi-Thread Iliac Screw assembly in claim 1 wherein the fastener enters the saddle through the saddle top and clips its head into the saddle inner spherical chamber and whose threaded body extends from the saddle circular opening at the bottom.

3. The Multi-Thread Iliac Screw assembly in claim 1 wherein said lower constriction is comprised of a short extension that projects downward at an angle to said circular lower opening wherein the upper section of said short extension retains said fastener in the inner chamber and wherein the fastener head rotates in the saddle inner chamber through broad angles up to 70 degrees by virtue of said short extensions downward projection at an angle thereby allowing placement of said saddle and said fastener at said anchoring point.

4. The Multi-Thread Iliac Screw assembly in claim 1 wherein said connector locking screw locks said vertebral rod into place.

5. The Multi-Thread Iliac Screw assembly in claim 1 wherein said saddle locking screw is designed as a cylindrical element with an external thread for threading with the saddle bore inner thread, a hexagonal key on top for reception of a screwdriver hexagonal tip to drive said saddle locking screw into said saddle from the top of said saddle and a lower curved surface.

6. The Multi-Thread Iliac Screw assembly in claim 1 wherein said saddle locking screw is used to hold the fastener in place by direct contact with said lower curved surface of said saddle locking screw wherein said lower curved surface exerts a force on said head of said fastener so that said fastener remains rigidly stationary with respect to said saddle once said fastener is driven into bone tissue at any angle with respect to the longitudinal axis of said saddle.

7. The Multi-Thread Iliac Screw assembly in claim 1 wherein said fastener is configured to fasten into Iliac bone tissue and is comprised of a head, a body with three threads each having a different pitch, a shaft that connects the threaded body to the head through a curved neck, and a tapered tip wherein the crest of each thread elongates from 3 mm to at least 6 mm from the body of said fastener to increase the surface area of the crest and thereby the frictional forces between Iliac bone tissue and each crest wherein the upper side of each crest is planar wherein the underside of each crest is curved which together with said planar upper side creates a termination edge that is approximately between two tenths of a millimeter to one millimeter in thickness to allow for deep cutting into Iliac bone tissue and wherein the lower thread of said fastener is configured for embedding in the lower rigid tissue of the Iliac bone, the middle thread of said fastener is configured for embedding in the middle porous tissue of the Iliac bone and the top thread of said fastener is configured for embedding in the top rigid tissue of the Iliac bone.

* * * * *